United States Patent
Maumela et al.

(10) Patent No.: US 9,533,922 B2
(45) Date of Patent: Jan. 3, 2017

(54) OLIGOMERISATION OF ETHYLENE TO MIXTURES OF 1-HEXENE AND 1-OCTENE

(71) Applicant: SASOL TECHNOLOGY (PROPRIETARY) LIMITED, Rosebank (ZA)

(72) Inventors: Munaka Christopher Maumela, Sasolburg (ZA); Moses Mokgolela Mogorosi, Sasolburg (ZA); Molise Stephen Mokhadinyana, Sasolburg (ZA); Matthew James Overett, Johannesburg (ZA); Kevin Blann, Johannesburg (ZA); Cedric Wahl Holzapfel, Randburg (ZA)

(73) Assignee: Sasol Technology (Proprietary) Limited, Rosebank (ZA)

( * ) Notice: Subject to any disclaimer, the term of this patent is extended or adjusted under 35 U.S.C. 154(b) by 0 days.

(21) Appl. No.: 14/888,520

(22) PCT Filed: May 6, 2014

(86) PCT No.: PCT/IB2014/061232
§ 371 (c)(1),
(2) Date: Nov. 2, 2015

(87) PCT Pub. No.: WO2014/181247
PCT Pub. Date: Nov. 13, 2014

(65) Prior Publication Data
US 2016/0083311 A1    Mar. 24, 2016

(30) Foreign Application Priority Data

May 9, 2013 (ZA) ................................ 2013/03362

(51) Int. Cl.
C07C 2/32 (2006.01)
C07C 2/36 (2006.01)

(52) U.S. Cl.
CPC . *C07C 2/32* (2013.01); *C07C 2/36* (2013.01); *C07C 2531/14* (2013.01); *C07C 2531/18* (2013.01); *C07C 2531/24* (2013.01); *C07C 2531/34* (2013.01)

(58) Field of Classification Search
CPC .......... C07C 2/32; C07C 2/38; C07C 2531/14; C07C 2531/18; C07C 2531/24; C07C 2531/34
See application file for complete search history.

(56) References Cited

U.S. PATENT DOCUMENTS

| 2006/0229480 A1* | 10/2006 | Blann et al. ........... B01J 31/143 585/535 |
| 2010/0190939 A1* | 7/2010 | Fritz et al. ............. B01J 31/143 526/126 |
| 2012/0316303 A1* | 12/2012 | Hanton et al. ............ C07C 2/32 526/133 |

FOREIGN PATENT DOCUMENTS

| WO | 2004/056479 A1 | 7/2004 |
| WO | 2009/006979 A2 | 1/2009 |

OTHER PUBLICATIONS

Van Leeuwen et al, "New processes for the selective production of 1-octene", Coordination Chemistry Reviews, Oct. 4, 2010, pp. 1499-1517, vol. 255, No. 13, Elsevier Science, Amsterdam, NL.

\* cited by examiner

*Primary Examiner* — Nathan M Nutter
(74) *Attorney, Agent, or Firm* — Whitham, Curtis & Cook, P.C.

(57) ABSTRACT

A process for the oligomerization of ethylene to predominantly 1-hexene or 1-octene or mixtures of 1-hexene and 1-octene includes contacting ethylene with a catalyst under ethylene oligomerization conditions. The catalyst comprises a source of chromium, a diphosphine ligating compound, and optionally an activator. The diphosphine ligating compound includes at least one optionally substituted fused cyclic structure including at least two rings, the optionally substituted fused cyclic structure including a 5- to 7-membered aromatic first ring bonded to a phosphorus atom, the aromatic first ring being fused to a 4- to 8-membered heterocyclic second ring, the heterocyclic second ring including a heteroatom which is separated by two ring atoms along the shortest connecting path from the phosphorous atom that is bonded to the first aromatic ring.

21 Claims, No Drawings

OLIGOMERISATION OF ETHYLENE TO MIXTURES OF 1-HEXENE AND 1-OCTENE

TECHNICAL FIELD

This invention relates to the oligomerisation of ethylene to mixtures of predominantly 1-hexene and 1-octene, in particular in the presence of an activated chromium catalyst with novel diphosphine ligands.

BACKGROUND OF THE INVENTION

It is known that chromium-based catalyst systems with diphosphine ligands catalyse the selective conversion of ethylene to 1-hexene and/or 1-octene depending on the reaction conditions and choice of ligand structure. In particular, the nature and position of any substituents on the aryl rings connected to the phosphines are crucial influences on the selectivity split between 1-hexene and 1-octene. Of particular interest to industry are catalysts for ethylene tetramerisation, as these catalysts are relatively rare. Octene is a valuable co-monomer for the production of high performance linear low density polyethylenes and elastomers, and few selective on-purpose routes to this chemical are known in industry. By comparison, catalysts for ethylene trimerisation are relatively common, and are used industrially by several companies. By tetramerisation it is meant that at least 30% 1-octene is produced in the process. By trimerisation it is meant that more than 70% 1-hexene is produced.

Non-limiting examples of selective ethylene oligomerisation catalyst systems include the ubiquitous Cr/bis(phosphino)amine (i.e. 'PNP') systems, particularly of the type $(Ar^1)(Ar^2)PN(R)P(Ar^3)(Ar^4)$, where $Ar^1$ to $Ar^4$ are aryl groups such as phenyl and R is a hydrocarbyl or a heterohydrocarbyl group, beginning with PNP ligands containing no substituents on the phenyl rings bonded to the P-atoms (e.g. as described in WO 2004/056479) and those with m- or p-methoxy groups on the phenyl rings (e.g. as described in WO 2004/056480). In addition to this, PNP systems containing o-fluoro groups on the phenyl rings are described in US 2008/0242811 and US 2010/0081777, and PNP systems bearing pendant donor atoms on the nitrogen linker are described in WO 2007/088329. Multi-site PNP ligands are discussed in US 2008/0027188. In addition to the Cr/PNP systems, chromium systems bearing N,N-bidentate ligands (e.g. as described in US 2006/0247399) can be used. PNP ligands with alkylamine or phosphinoamine groups bonded to one of the PNP phosphines (i.e. 'PNPNH' and 'PNPNP' ligands) are described in WO 2009/006979. Finally, carbon bridged diphosphine (i.e. 'PCCP' ligands) are described in WO 2008/088178 and WO 2009/022770.

Related ethylene trimerisation catalysts with high selectivity for 1-hexene can be obtained by using PNP ligands with ortho-methoxy or ortho-alkyl substituents on the phenyl rings bonded to the P-atoms (e.g. as described in WO2002/04119, WO2004/056477 and WO2010/034101).

The above catalyst systems suffer from a number of shortcomings. These include low catalyst activity and high polymer co-product formation when operated at elevated temperatures, especially above 80° C., and high selectivity towards heavy oligomers (C10 to C30+ olefins). These problems are especially evident for tetramerisation catalysts, where the challenge of obtaining good catalyst performance together with good selectivity towards 1-octene at high reaction temperatures is severe.

In a recent review article describing catalyst systems for ethylene tetramerisation, van Leeuwen et al (Coordination Chemistry Reviews, 255, (2011), 1499-1517) have discussed the problems associated with elevated reaction temperatures. They state that: "In general the selective ethylene tetramerisation experiments are performed in the temperature range 40-60° C. Various studies on both semi-batch and continuous miniplant have shown a strong dependency of the reaction temperature on the activity and selectivity of the $Cr(III)/Ph_2N(R)PPh_2$/MAO catalytic system. High reaction temperatures (>60° C.) significantly reduced the catalyst productivity as compared to reactions performed at lower temperature under the same ethylene pressure. Consequently catalyst decomposition with increasing temperature is probably the main reason for lower productivities at high temperatures . . . "

When carrying out a process for tetramerisation of ethylene, the aim is to choose a catalyst system and adjust process conditions in order to produce the maximum amount of 1-octene, as opposed to trimerisation processes where catalysts and process conditions are adjusted to produce the maximum amount of 1-hexene. 1-Hexene is also typically co-produced in a tetramerisation process and it is well known in the art of the invention that higher temperatures shift the selectivity from 1-octene towards 1-hexene. Apart from 1-octene and 1-hexene, which are typically the targeted products in a selective oligomerisation process, various other co-products are formed in tetramerisation reactions, notably heavy (C10+) oligomers predominantly formed by secondary reactions of 1-hexene or 1-octene with ethylene. Tetramerisation catalysts which minimize the formation of these unwanted co-products are highly desirable.

Furthermore, the formation of a high molecular weight polymer co-product by the Cr-based ethylene tetramerisation catalyst may present a major technical challenge when commercialising an ethylene tetramerisation process as polymer fouling reduces plant run time and necessitates shut-downs due to blockages and difficult temperature control. When running tetramerisation processes at reaction temperatures in the range of 40 to 80° C., the polymer precipitates out of solution in the reactor, which brings risk to the process due to the possibility of reactor or downstream equipment fouling.

Consequently, new catalyst systems which can operate with good rates, low polymer formation, good 1-octene to 1-hexene ratios and reduced selectivity to heavy oligomers are highly desirable. Such catalysts would be useful at oligomerisation temperatures of 40 to 80° C., by reducing the amount of unwanted co-products formed, including polyethylene and heavy oligomers. Alternatively, they could be useful at higher oligomerisation reaction temperatures, where the polymer co-product remains in solution, but where catalyst stability and adequate selectivity to 1-octene are the greatest challenges.

SUMMARY OF THE INVENTION

According to one aspect of the invention there is provided a process for the oligomerisation of ethylene to predominantly 1-hexene or 1-octene or mixtures of 1-hexene and 1-octene, the process including contacting ethylene with a catalyst under ethylene oligomerisation conditions, said catalyst comprising:

i) a source of chromium;
ii) a ligating compound of the formula

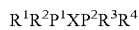

wherein $P^1$ and $P^2$ are phosphorus atoms;
X is a linking group between $P^1$ and $P^2$; and
$R^1$ to $R^4$ are independently a hydrocarbyl group, an organoheteryl group or a heterohydrocarbyl group, wherein at least one of $R^1$, $R^2$, $R^3$, and $R^4$ includes an optionally substituted fused cyclic structure including at least two rings, the optionally substituted fused cyclic structure including a 5- to 7-membered aromatic first ring bonded to the respective phosphorus atom, the aromatic first ring being fused to a 4- to 8-membered heterocyclic second ring, the heterocyclic second ring including a heteroatom, the heteroatom being separated from the respective phosphorous atom by two ring atoms along the shortest path; and
iii) optionally a catalyst activator or combination of catalyst activators.

According to some embodiments of the invention there is provided a process for the oligomerisation of ethylene to predominantly 1-hexene or 1-octene or mixtures of 1-hexene and 1-octene, the process including contacting ethylene with a catalyst under ethylene oligomerisation conditions, said catalyst comprising:
i) a source of chromium;
ii) a ligating compound of the formula

wherein $P^1$ and $P^2$ are phosphorus atoms;
X is a linking group between $P^1$ and $P^2$; and
$R^1$ to $R^4$ are independently a hydrocarbyl group, an organoheteryl group or a heterohydrocarbyl group, wherein at least one of $R^1$, $R^2$, $R^3$, and $R^4$ can be represented as Z, where Z includes a fused bicyclic structure including an optionally substituted six-membered aromatic ring fused to an optionally substituted 4- to 8-membered heterocyclic second ring, and which can be represented as:

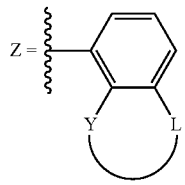

such that Y=O, S, P, N or $NR^5$, where $R^5$ includes hydrogen, halogen, hydrocarbyl, organoheteryl, heterohydrocarbyl or polar groups; and
L is a linking group between Y and the six-membered aromatic ring; and
iii) optionally a catalyst activator or combination of catalyst activators.

DETAILED DESCRIPTION OF EMBODIMENTS OF THE INVENTION

The invention relates to a process for the oligomerisation of ethylene to predominantly 1-hexene or 1-octene or mixtures of 1-hexene and 1-octene, the process including contacting ethylene with a catalyst under ethylene oligomerisation conditions, said catalyst comprising a source of chromium, a diphosphine ligating compound, which diphosphine ligating compound includes at least one optionally substituted fused cyclic structure including at least two rings, the optionally substituted fused cyclic structure including a 5- to 7-membered aromatic first ring bonded to a phosphorus atom, the aromatic first ring being fused to a 4- to 8-membered heterocyclic second ring, the heterocyclic second ring including a heteroatom which is separated by two ring atoms along the shortest connecting path from the phosphorous atom that is bonded to the first aromatic ring, and optionally an activator.

In the specification, the following definitions apply:

A "hydrocarbyl group" as per IUPAC includes a univalent group formed by removing one hydrogen atom from a hydrocarbon;

A "heterohydrocarbyl group" as defined herein is a univalent group formed by removing one hydrogen atom from a carbon atom of a heterohydrocarbon, that is a hydrocarbon compound which includes at least one hetero atom (that is, not being H or C), and which group covalently bonds with one other moiety through the resultant free valency on that carbon atom;

An "organoheteryl group" as per IUPAC includes univalent groups containing carbon, which are thus organic, but which have their free valence at an atom other than carbon;

A "hydrocarbylene group" as per IUPAC includes divalent groups formed by removing two hydrogen atoms from a hydrocarbon, the free valencies of which are not engaged in a double bond;

A "heterohydrocarbylene group" as defined herein is a divalent group formed by removing two hydrogen atoms from either one or two carbon atoms of an organic molecule containing at least one heteroatom, the free valencies of which are not engaged in a double bond.

Chromium Source (i):

Any source of chromium that allows the oligomerisation to proceed may be used. The source of chromium may be an inorganic salt, an organic salt, a coordination compound or an organometallic complex.

In some embodiments the source of chromium is selected from the group consisting of chromium trichloride tristetrahydrofuran complex; (benzene)tricarbonyl chromium; chromium (III) octanoate; chromium hexacarbonyl; chromium (III) acetylacetonate; chromium (III) naphthenate; chromium (III) 2-ethylhexanoate; chromium (III) acetate; chromium (III) 2,2,6,6-tetramethylheptadionate; chromium (III) chloride. In some embodiments it is chromium (III) acetylacetonate or chromium (III) 2-ethylhexanoate.

The chromium source may be introduced to the process as a coordination complex of the ligating compound. However, for reasons of cost and commercial operability, in some embodiments the ligating compound and chromium source are added as separate components to the process. Catalyst systems which give good catalyst performance only when an isolable chromium-ligand coordination complex is used therefore suffer a disadvantage to catalyst systems which can be prepared by mixing a chromium source and ligand in the process.

Ligating Compound (ii):
Linking Group X

X may be selected from the group consisting of an organic linking group such as a hydrocarbylene, heterohydrocarbylene; an inorganic linking group comprising either a single- or two-atom linker spacer; and a group comprising dimethylmethylene, ethane-1,2-diyl, ethene-1,2-diyl, propane-1,2-diyl, propane-1,3-diyl, cyclopropane-1,1-diyl, cyclopropane-1,2-diyl, butane-2,3-diyl, cyclobutane-1,2-diyl, cyclopentane-1,2-diyl, cyclohexane-1,2-diyl, cyclohexane-1,1-diyl, 1,2-phenylene, naphthalene-1,8-diyl, phenanthrene-9,10-diyl, phenanthrene-4,5-diyl, 9,10-anthracene-diyl, 1,2-catecholate, 1,2-diarylhydrazine-1,2-diyl (—N(Ar)—N(Ar)— where Ar is an aryl group), 1,2-dialkylhydrazine-1,2-diyl (—N(Alk)-N(Alk)- where Alk is an alkyl or a cycloalkyl group), 1-alkyl-2-arylhydrazine-1,2-diyl (—N(Alk)-N(Ar)— where Alk is an alkyl or a cycloalkyl group and Ar is an aryl group), —N(R')—X$^1$—N(R")— where R' and R" are independently alkyl, cycloalkyl or aryl groups and X$^1$ is a hydrocarbylene group, —B(R$^5$)—, —Si(R$^5$)$_2$—, —P(R$^5$)— and —N(R$^5$)— where R$^5$ is a hydrocarbyl group, an organoheteryl group or a heterohydrocarbyl group. Preferably R$^5$ is a hydrocarbyl group or a heterohydrocarbyl group.

In some embodiments X consists of —N(R$^6$)—, —N(R$^6$)—N(R$^7$)—, —C(R$^{8a}$)(R$^{8b}$)—N(R$^6$)— or a hydrocarbylene, where R$^6$ and R$^7$ are independently a hydrocarbyl group, a heterohydrocarbyl group or an organoheteryl group and R$^{8a}$ and R$^{8b}$ are independently a hydrogen, a hydrocarbyl group, a heterohydrocarbyl group or an organoheteryl group. In some embodiments R$^6$, R$^7$, R$^{8a}$ and R$^{8b}$ may be an alkyl, cycloalkyl, substituted alkyl, substituted cycloalkyl, aryl, substituted aryl, aryloxy, substituted aryloxy, alkoxycarbonyl, carbonyloxy, alkoxy, aminocarbonyl, carbonylamino, dialkylamino, pyrolyl, silyl group or derivative thereof, and aryl substituted with any of these substituents. In some embodiments R$^6$, R$^7$, R$^{8a}$ and R$^{8b}$ may be an alkyl, cycloalkyl, substituted alkyl, substituted cycloalkyl, aryl, substituted aryl, dialkylamino, silyl group or derivative thereof, and R$^{8a}$ and R$^{8b}$ may additionally be hydrogen. In some embodiments R$^6$, R$^7$, R$^{8a}$ and R$^{8b}$ may be an alkyl, cycloalkyl, substituted alkyl, substituted cycloalkyl, aryl, substituted aryl, and R$^{8a}$ and R$^{8b}$ may additionally be hydrogen. In some embodiments, R$^6$, R$^7$, R$^{8a}$ and R$^{8b}$ consist of hydrocarbyl groups, such as methyl, ethyl, propyl, allyl, isopropyl, cyclopropyl, butyl, tertiary-butyl, sec-butyl, cyclobutyl, pentyl, isopentyl, 1,2-dimethylpropyl(3-methyl-2-butyl), 1,2,2-trimethylpropyl(R/S-3,3-dimethyl-2-butyl), 1-(1-methylcyclopropyl)-ethyl, neopentyl, cyclopentyl, cyclohexyl, hexyl, cycloheptyl, cyclo-octyl, decyl, cyclodecyl, 1,5-dimethylheptyl, 1-methylheptyl, 2-naphthylethyl, 1-naphthylmethyl, adamantylmethyl, 1-adamantyl, 2-adamantyl, 2-isopropylcyclohexyl, 2,6-dimethylcyclohexyl, cyclododecyl, 2-methylcyclohexyl, 3-methylcyclohexyl, 4-methylcyclohexyl, 2-ethylcyclohexyl, 2-isopropylcyclohexyl, 2,6-dimethyl-cyclohexyl, exo-2-norbornanyl, (1,1'-bis(cyclohexyl)-4,4'-methylene), 1,6-hexylene, 1-naphthyl, 2-naphthyl, diphenylmethyl, 1,2-diphenyl-ethyl, phenylethyl, 2-methylphenyl, 3-methylphenyl, 4-methylphenyl, 2,6-dimethyl-phenyl, or a 1,2,3,4-tetrahydronaphthyl, and R$^{8a}$ and R$^{8b}$ may additionally be hydrogen.

X, in some embodiments, is —N(R$^9$)—, where R$^9$ is a hydrocarbyl group, a heterohydrocarbyl group or an organoheteryl group. In some embodiments R$^9$ is a hydrocarbyl group or a heterohydrocarbyl group. In some embodiments R$^9$ is an alkyl, cycloalkyl or aryl group. In some preferred embodiments R$^9$ is an alkyl or cycloalkyl group. In some embodiments R$^9$ is an alkyl group of the form —CH$_2$R$^{10}$, where R$^{10}$ is hydrogen or an alkyl group or a cycloalkyl group. In some embodiments R$^9$ is methyl or a linear alkyl group.

Nature of the Groups R$^1$-R$^4$

R$^1$ to R$^4$ are independently a hydrocarbyl, an organoheteryl group or a heterohydrocarbyl group, such that at least one of R$^1$, R$^2$, R$^3$, and R$^4$ includes an optionally substituted fused cyclic structure including at least two rings, the optionally substituted fused cyclic structure including a 5- to 7-membered aromatic first ring bonded to the respective phosphorus atom, the aromatic first ring being fused to a 4- to 8-membered heterocyclic second ring, the heterocyclic second ring including a heteroatom which is separated by two ring atoms along the shortest connecting path from the phosphorous atom that is bonded to the first aromatic ring.

In some embodiments R$^1$ to R$^4$ all include aromatic moieties directly bonded to P$^1$ or P$^2$. In some embodiments, any of the R$^1$ to R$^4$ groups that are not the fused cyclic structure as described in the paragraph above are phenyl groups which are optionally substituted. Any of R$^1$ to R$^4$ that are not fused cyclic structures as described in the paragraph above may be linked together, for example to form a dibenzophosphol-5-yl group together with either P$^1$ or P$^2$.

Nature of the Groups R$^1$-R$^4$ that are Fused Cyclic Groups

R$^1$ to R$^4$ are independently a hydrocarbyl, an organoheteryl group or a heterohydrocarbyl group, such that at least one of R$^1$, R$^2$, R$^3$, and R$^4$ includes an optionally substituted fused cyclic structure including at least two rings, the optionally substituted fused cyclic structure including a 5- to 7-membered aromatic first ring bonded to the respective phosphorus atom, the aromatic first ring being fused to a 4- to 8-membered heterocyclic second ring, the heterocyclic second ring including a heteroatom which is separated by two ring atoms along the shortest connecting path from the phosphorous atom that is bonded to the first aromatic ring.

In some embodiments of the invention, the optionally substituted aromatic first ring directly bonded to the respective phosphorous atom is a 5-or 6-membered aromatic ring. In some embodiments, it is a 6-membered aromatic ring.

In some embodiments of the invention, at least one of R$^1$, R$^2$, R$^3$, and R$^4$ can be represented as Z, where Z can be represented as:

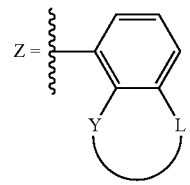

such that Y=O, S, P, N or NR$^5$, where R$^5$ includes hydrogen, halogen, hydrocarbyl, organoheteryl, heterohydrocarbyl or polar groups;

L is a linking group between Y and the six-membered aromatic ring; and the heterocyclic ring including Y and L is a 4- to 8-membered heterocyclic ring.

In some embodiments of the invention, Y is an oxygen, sulfur or nitrogen atom. In some embodiments, Y is an oxygen or sulfur atom. In some embodiments, Y is an oxygen atom.

In some embodiments of the invention, L is selected such that Z is an optionally substituted fused bicyclic heteroaryl group incorporating Y as a ring atom of this bicyclic heteroaryl group, where the ring including Y is a 5- or 6-membered ring.

In some embodiments of the invention, L is selected from the group comprising a hydrocarbylene group, —N=N— and —CR$^7$=N—, where R$^7$ is a hydrogen, hydrocarbyl or heterohydrocarbyl group.

In some embodiments of the invention, L is chosen such that Z is an optionally substituted fused bicyclic heteroaryl group including further fused ring structures to form a fused polycyclic structure with more than two rings.

In some embodiments of the invention, Z is selected from the group consisting of optionally substituted 1-benzofuran-7-yl, 5-dibenzofuran-4-yl, 1-benzothiophen-7-yl, quinol-8-yl, indol-7-yl and 8-benzophosphabenzene.

In some embodiments of the invention, Z is selected from the group consisting of optionally substituted 1-benzofuran-7-yl, 5-dibenzofuran-4-yl, 1-benzothiophen-7-yl, quinol-8-yl.

In some embodiments of the invention, Z is an optionally substituted 1-benzofuran-7-yl group, an optionally substituted 1-benzothiophen-7-yl group or an optionally substituted 5-dibenzofuran-4-yl-group.

In some embodiments of the invention, Z is an optionally substituted 1-benzofuran-7-yl group or an optionally substituted 5-dibenzofuran-4-yl group.

In some embodiments of the invention Z is an optionally substituted 5-dibenzofuran-4-yl group.

Number and Substitution Pattern of the $R^1$-$R^4$ Groups Including a Fused Bicyclic Group $R^1$ to $R^4$ are independently a hydrocarbyl, an organoheteryl group or a heterohydrocarbyl group, such that at least one of $R^1$, $R^2$, $R^3$, and $R^4$ includes an optionally substituted fused cyclic structure including at least two rings, the optionally substituted fused cyclic structure including a 5- to 7-membered aromatic first ring bonded to the respective phosphorus atom, the aromatic first ring being fused to a 4- to 8-membered heterocyclic second ring, the heterocyclic second ring including a heteroatom which is separated by two rings atoms along the shortest connecting path from the phosphorous atom bonded to the first aromatic ring. In some embodiments no more than two of $R^1$ to $R^4$ include such a fused cyclic structure. In some embodiments, $R^1$ and $R^2$ both include such a fused cyclic structure. In some embodiments, only one of $R^1$, $R^2$, $R^3$, and $R^4$ includes such a fused cyclic structure.

Other Considerations

Any one of $R^1$ to $R^4$ may independently be linked to one or more of each other, or to X, to form a cyclic structure.

In some embodiments, the $R^1$ to $R^4$ groups including a fused cyclic structure do not incorporate the phosphorous atom to which it is bonded as a ring atom of the fused cyclic structure.

The ligating compound may also include multiple $R^1R^2P^1XP^2R^3R^4$ units. Non-limiting examples of such ligands include dendrimeric ligands as well as ligands where the individual units are coupled either via one or more of the $R^1$-$R^4$ groups or via the linking group X.

It will be appreciated that a diphosphinoimine compound of the form $R^1R^2P^1$—$P^2$(=$NR^9$)$R^3R^4$ ('P—P=N') is a rearranged isomer of the diphosphinoamine compound $R^1R^2P^1N(R^9)P^2R^3R^4$ ('P—N—P') claimed in the present invention, as shown by Dyson et al in Inorganica Chimica Acta 359 (2006) 2635-2643. Regardless of the structural formulation of the ligating compound in its pure and isolated form, its use will fall under the present invention if it exists in the 'P—N—P' form when used in a tetramerisation process.

In some embodiments the ligating compound may be one of:

(1-benzofuran-7-yl)$_2$PN(n-butyl)P(phenyl)$_2$; (1-benzofuran-7-yl)(phenyl)PN(n-butyl)P(phenyl)$_2$;
(1-benzofuran-7-yl)$_2$PN(n-butyl)(dibenzophosphol-5-yl); (1-benzofuran-7-yl)(phenyl)PN(n-butyl)(dibenzophosphol-5-yl);
(1-benzofuran-7-yl)$_2$PN(n-hexyl)P(phenyl)$_2$; (1-benzofuran-7-yl)(phenyl)PN(n-hexyl)P(phenyl)$_2$;
(1-benzofuran-7-yl)$_2$PN(isobutyl)P(phenyl)$_2$; (1-benzofuran-7-yl)(phenyl)PN(isobutyl)P(phenyl)$_2$;
(1-benzofuran-7-yl)$_2$PN(isopropyl)P(phenyl)$_2$; (1-benzofuran-7-yl)(phenyl)PN(isopropyl)P(phenyl)$_2$;
(1-benzofuran-7-yl)$_2$PN(1,2-dimethylpropyl)P(phenyl)$_2$; (1-benzofuran-7-yl)(phenyl)PN(1,2-dimethylpropyl)P(phenyl)$_2$;
(1-benzofuran-7-yl)$_2$PN(n-butyl)(furan-2-yl)$_2$; (1-benzofuran-7-yl)(phenyl)PN(n-butyl)P(furan-2-yl)$_2$;
(1-benzofuran-7-yl)$_2$PN(n-butyl)P(furan-3-yl)$_2$; (1-benzofuran-7-yl)(phenyl)PN(n-butyl)P(furan-3-yl)$_2$;
(1-benzofuran-7-yl)$_2$PN(n-butyl)P(pyrid-2-yl)$_2$; (1-benzofuran-7-yl)(phenyl)PN(n-butyl)P(pyrid-2-yl)$_2$;
(1-benzofuran-7-yl)$_2$PN(n-butyl)P(pyrid-4-yl)$_2$; (1-benzofuran-7-yl)(phenyl)PN(n-butyl)P(pyrid-4-yl)$_2$;
(1-benzofuran-7-yl)$_2$PN(n-butyl)P(pyrid-3-yl)$_2$; (1-benzofuran-7-yl)(phenyl)PN(n-butyl)P(pyrid-3-yl)$_2$;
(1-benzofuran-7-yl)$_2$PN(n-butyl)P(1-benzofuran-7-yl)$_2$; (1-benzofuran-7-yl)$_2$PN(methyl)P(1-benzofuran-7-yl)$_2$;
(1-benzothiophen-7-yl)$_2$PN(n-hexyl)P(phenyl)$_2$; (1-benzothiophen-7-yl)(Phenyl)PN(n-hexyl)P(phenyl)$_2$;
(1-indol-7-yl)$_2$PN(n-butyl)P(phenyl)$_2$; (1-indol-7-yl)(phenyl)PN(n-butyl)P(phenyl)$_2$;
(1-quinol-8-yl)$_2$PN(n-butyl)P(phenyl)$_2$; (1-quinol-8-yl)(phenyl)PN(n-butyl)P(phenyl)$_2$;
(1-benzothiophen-7-yl)$_2$PN(n-butyl)(dibenzophosphol-5-yl); (1-benzothiophen-7-yl)(phenyl)PN(n-butyl)(dibenzophosphol-5-yl);
(5-dibenzofuran-4-yl)$_2$PN(n-Hex)P(phenyl)$_2$; (5-dibenzofuran-4-yl)(phenyl)PN(n-Hex)P(phenyl)$_2$;
(5-dibenzofuran-4-yl)$_2$PN(n-Hex)(dibenzophosphol-5-yl); (5-dibenzofuran-4-yl)(phenyl)PN(n-Hex)(dibenzophosphol-5-yl);
(1-benzofuran-7-yl)$_2$PN(Me)N(Me)P(phenyl)$_2$; (1-benzofuran-7-yl)(phenyl)PN(Me)N(Me)P(phenyl)$_2$;
(1-benzofuran-7-yl)$_2$PN(Me)N(Me)dibenzophosphol-5-yl); (1-benzofuran-7-yl)(phenyl)PN(Me)N(Me)(dibenzophosphol-5-yl);
(1-benzofuran-7-yl)$_2$P(1,2-phenylene)P(phenyl)$_2$; (1-benzofuran-7-yl)(phenyl(1,2-phenylene)P(phenyl)$_2$;
(1-benzofuran-7-yl)$_2$P(1,2-phenylene)(dibenzophosphol-5-yl); (1-benzofuran-7-yl)(phenyl)P(1,2-phenylene)(dibenzophosphol-5-yl);
(1-benzofuran-7-yl)$_2$PCH$_2$N(napthyl)(dibenzophosphol-5-yl); (1-benzofuran-7-yl)(phenyl)PCH$_2$N(napthyl)(dibenzophosphol-5-yl);
(1-benzofuran-7-yl)$_2$PCH$_2$N(napthyl)P(phenyl)$_2$; (1-benzofuran-7-yl)(phenyl)PCH$_2$N(napthyl)P(phenyl)$_2$;
(1-benzofuran-7-yl)$_2$PN(methyl)CH$_2$CH$_2$CH$_2$CH$_2$N(methyl)P(phenyl)$_2$;
(1-benzofuran-7-yl)$_2$PN(methyl)CH$_2$CH$_2$CH$_2$N(methyl)P(phenyl)$_2$.

Activator/Additives (iii):

The above process may include an activator to activate the catalyst. Such an activator is a compound that generates an active catalyst when the activator is combined with the catalyst. These activators may be the same or similar to those found to be useful for activating transition-metal-based olefin polymerisation catalysts, a review of which is provided by Marks [*Chem Rev.* 2000, 100, 1391-1394]. Mixtures of activators may also be used.

Suitable compounds include organoaluminum compounds, organoboron compounds and inorganic acids and salts, such as tetrafluoroboric acid etherate, silver tetrafluoroborate, sodium hexafluoroantimonate and the like. Suitable organoaluminum compounds include compounds of the formula $AlR_3$, where each R is independently $C_1$-$C_{12}$ alkyl, oxygen or halide, and compounds such as $LiAlH_4$ and the like. Examples include trimethylaluminum (TMA), triethylaluminum (TEA), tri-isobutylaluminium (TIBA), tri-n-octylaluminium, methylaluminium dichloride, ethylaluminium dichloride, dimethylaluminium chloride, diethylaluminium chloride, ethylaluminiumsesquichloride, methylaluminiumsesquichloride, and aluminoxanes. Aluminoxanes are well known in the art as typically oligomeric compounds which can be prepared by the controlled addition of water to an alkylaluminium compound, for example trimethylaluminium. Such compounds can be linear, cyclic, cages or mixtures thereof. Commercially available aluminoxanes are generally believed to be mixtures of linear and cyclic compounds. The cyclic aluminoxanes can be represented by the formula $[R^{11}AlO]_s$ and the linear aluminoxanes by the formula $R^{12}(R^{13}AlO)_s$ wherein s is a number from about 2 to 50, and wherein $R^{11}$, $R^{12}$, and $R^{13}$ represent hydrocarbyl groups, typically $C_1$ to $C_6$ alkyl groups, for example methyl, ethyl or butyl groups. Alkylaluminoxanes especially methylaluminoxane (MAO) are particularly suitable. (MAO is also referred to as methalumoxane and methylalumoxane in the literature).

It will be recognized by those skilled in the art that commercially available alkylaluminoxanes may contain a proportion of trialkylaluminium. For instance, commercial MAO usually contains approximately 10 wt % trimethylaluminium (TMA), and commercial "modified MAO" (or "MMAO") contains both TMA and TIBA. Quantities of alkylaluminoxane are generally quoted herein on a molar basis of aluminium (and include such "free" trialkylaluminium). The alkylaluminoxane and/or alkylaluminium may be added to the reaction media (i.e. ethylene and/or diluent and/or solvent) prior to the addition of the catalyst or at the same time as the catalyst is added. Such techniques are known in the art of oligomerization and are disclosed in more detail in for example, U.S. Pat. Nos. 5,491,272; 5,750,817; 5,856,257; 5,910,619; and 5,919,996 as well as WO 2008/146215 and WO 2007/007272.

In the preparation of the catalyst systems used in the present invention, the optimal quantity of activating compound to be employed is easily determined by simple testing, for example, by the preparation of small test samples which can be used to oligomerize small quantities of ethylene and thus to determine the activity of the produced catalyst. It is generally found for alkylaluminium and aluminoxane based activators or co-activators that a suitable quantity employed is 0.5 to 2000 moles of aluminium per mole of chromium.

Examples of suitable organoboron activator compounds are boroxines, $NaBH_4$, trimethylboron, triethyl boron, triphenylboron, dimethylphenylammoniumtetra(phenyl)borate, trityltetra(phenyl)borate, dimethyiphenylammonium tetrakis(pentafluorophenyl)borate, trityl tetrakis(pentafluorophenyl)borate, tris(pentafluorophenyl) boron, sodium tetrakis[(bis-3,5-trifluoromethyl)phenyl]borate, dimethylphenylammonium tetrakis[(bis-3,5-trifluoromethyl)phenyl] borate, and trityl tetrakis[(bis-3,5-trifluoromethyl)phenyl] borate.

Those skilled in the art will recognise that boron-containing activators are commonly used in combination with aluminium alkyl activators.

In some embodiments organoboron activators, as described in WO 2010/092554, include a cation and a non-coordinating anion of the general formula

wherein:
L* is an atom selected from the group consisting of N, S and P;
the cation $[(R)_xL^*-H]^+$ is a Bronsted acid;
x is an integer 1, 2 or 3;
each R is the same or different and each is a —H, hydrocarbyl group or a heterohydrocarbyl group;
provided that at least one of R comprises at least 6 carbon atoms and provided further that the total number of carbon atoms in $(R)_x$ collectively is greater than 12;
$R^{14}$ independently at each occurrence is selected from the group consisting of hydride, dialkylamido, halide, alkoxide, aryloxide, hydrocarbyl, halosubstituted-hydrocarbyl radicals, halosubstituted-alkoxide, halosubstituted-aryloxide and a halosubstituted aromatic moiety with at least one halide substituent on the aromatic moiety.

Illustrative, but non-limiting examples of these organoboron activators include methyldi(octadecyl)ammonium tetrakis(pentafluorophenyl)borate and trioctylammonium tetrakis(pentafluorophenyl)borate.

The source of chromium and the organoboron activator may be combined in proportions to provide organoboron compound/chromium molar ratios from about 0.1 to 50 organoboron to 1 chromium, or from about 0.8 to 20 organoboron to 1 chromium, or from 1 to 10 organoboron to 1 chromium.

In some embodiments activators, as described in WO 2007/039851, include a cation and an anion component, and may be represented by the following formula:

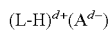

where L is a neutral Lewis base; H is hydrogen; $(L-H)^{d+}$ is a Bronsted acid; $A^{d-}$ is a non-coordinating anion having the charge $d^-$; and d is an integer from 1 to 3.

In these activator compounds, $A^{d-}$ can be a fluorinated aluminate group. Illustrative but non-limiting examples of the anion component $A^{d-}$ are $[Al\{OC(CF_3)_3\}_4]^-$; $[Al(OC_6F_5)_4]^-$; $[Al(C_6F_4O_2)_2]^-$; $[AlF\{OC(CF_3)_3\}_3]^-$; $[Al_2F\{OC(CF_3)_3\}_6]^-$; and $[Ta(OC_6F_5)_6]^-$.

The activator compound may optionally be a solid material, or be supported on an insoluble solid material. For example, aluminoxanes such as MAO and borate activators may be supported on inorganic oxides such as alumina, silica, $MgCl_2$ or the like.

The process may further include the use of compounds that may act as a reducing or oxidising agent, such as sodium or zinc metal and the like, or an oxygen-containing compound, for example oxygen and the like. Additionally, hydrogen ($H_2$) and/or silanes and the like may be used in the catalytic composition or otherwise added to the process. The process may also include the use of a zinc species as an additive, as described in WO 2011/048527, which is herein incorporated by reference. Preferred zinc species would be dialkyl zinc reagents such as dimethylzinc or diethylzinc.

Catalyst Preparation:

The chromium (i) and ligand (ii) may be present in any molar ratio which produces oligomer, and in some embodiments is between 100:1 and 1:100, or from 10:1 to 1:10, or from 3:1 to 1:3. Generally the amounts of (i) and (ii) are approximately equal, i.e. a ratio of between 1.5:1 and 1:1.5.

The ligand, chromium and activators of the catalyst system utilized in the present Invention may be added together simultaneously or sequentially, in any order, and in the presence or absence of ethylene in any suitable solvent at any suitable concentration, so as to give an active catalyst. For example, the ligand, chromium, activators and ethylene may be contacted together simultaneously; or the ligand, chromium and activators may be added together simultaneously or sequentially in any order and then contacted with ethylene; or chromium and the ligand may be added together to form an isolable metal-ligand complex and then added to the activator and contacted with ethylene; or the ligand, chromium and activators/co-activators may be added together to form an isolable metal-ligand complex and then contacted with ethylene.

Any or all of the chromium source, ligating compound and activator components utilized in the present invention can be unsupported or supported on a support material, for example silica, alumina, $MgCl_2$ or zirconia, or on a polymer, for example polyethylene, polypropylene, polystyrene or poly(aminostyrene).

Diluent:

The process of the present invention may be carried out in the presence or absence of an added diluent. In some embodiments of the invention the diluents include oligomerisation products e.g. 1-octene and/or 1-hexene, aliphatic and aromatic hydrocarbon solvents and halogenated-aromatic solvents such as chlorobenzene, dichlorobenzene, fluorobenzene and the like. In some embodiments the diluents are aliphatic hydrocarbon solvents including but not limited to Isopar™, iso-octane, cyclohexane, cyclopentane, methylcyclohexane, propane, isobutane, isopentane, neopentane, 2-15 methylpentane, or 3-methylpentane.

Alternatively the process can be conducted as a bulk process in which essentially neat reactant and/or product olefins serve as the dominant medium.

Process Conditions:

The oligomerisation reaction may take place at any suitable temperature to allow oligomerisation to proceed. Suitable temperatures may be from 0° C. to 200° C. Preferred temperatures are dependent on the conditions employed.

In one embodiment, the oligomerisation is conducted under slurry phase conditions, which is herein taken to mean that a substantial portion of any polymer co-product is present in the solid phase, and not predominantly dissolved in the liquid reaction medium under the chosen reaction conditions. Suitable temperatures to achieve this range from 0° C. to about 80° C., for instance about 40° C. to about 80° C. Such process conditions may be chosen for optimal catalyst activity and selectivity.

In another embodiment, the oligomedrsation is conducted under solution phase conditions, which is herein taken to mean that any polymer co-product remains substantially dissolved in the liquid reaction medium under the chosen reaction conditions. Suitable temperatures to achieve this range from above 80° C. to about 130° C. In some embodiments the temperature range is between 85° C. and 130° C., whilst in other embodiments the temperature range is between 90° C. and 110° C. Such process conditions may be chosen to reduce fouling of the reactor or other process equipment.

Surprisingly, the catalysts of the present invention have been found to offer benefits over other catalysts known in the art, under both slurry phase and solution phase conditions.

Under slurry phase conditions, the catalysts of the present invention have extremely high activities, low polymer co-product formation and/or reduced selectivities to unwanted heavy oligomers (C10+), while retaining good selectivity towards 1-octene, a particularly favoured product.

Under solution phase conditions, the catalysts of the present invention are found to be highly active, with low polymer formation, above 80° C. Even more surprisingly, these catalysts are still highly active, with low polymer formation, above 90° C. Not wishing to be bound by theory, the catalysts of the present invention are less susceptible to the thermally induced catalytic decomposition pathways, as discussed by van Leeuwen.

Suitable reaction pressures are from atmospheric to 800 atmospheres (bar), or from 5 atmospheres to 100 atmospheres, or from 40 to 100 atmospheres, or from 60 to 100 atmospheres. It was demonstrated that the negative effect of higher reaction temperatures on selectivity towards 1-octene can be reversed through the use of higher reaction pressures, together with the catalysts and reaction temperature ranges of the present invention.

There exist a number of options for the tetramerisation reactor including batch, semi-batch, and continuous operation. In some embodiments the process is a continuous process, in which case reactors utilizing both CSTR and plug flow behavior may be considered. There are different potential configurations as a subset of these two types of reactors. For example, CSTR type reactors include bubble columns, stirred tanks, loop reactors with single or two phases while plug flow reactors include fixed bed and homogeneous tubular types of varying residence times. As a further subset, reactors can be configured with different cooling options such as internal or external heat exchangers, interstage coolers, and cold feed heat removal amongst others. All configurations can be run in continuous or batch mode, and there is opportunity to configure the same reactor several times in series or use combinations of different reactor types and cooling techniques together to achieve the desired result.

For systems where tetramerisation takes place in the liquid phase, different mass transfer opportunities exist including jet loop mixing, bubble column sparging, tubular reactor multiple injections and pre-saturation of the feed material amongst others.

The reactor type selected may depend on factors such as heat removal, mechanical robustness with regard to fouling, residence time distributions, product composition effects as a result of secondary reactions and mechanical equipment cost Implications. In a slurry phase process where polymer precipitates out of the reaction medium, the selection criteria of heat removal and mechanical robustness with regard to fouling may be expected to dominate and many reactor configurations may therefore be excluded. In a solution phase process, a wider range of reactor configurations may be considered and implemented to optimize factors such as residence time distributions, product composition effects as a result of secondary reactions and mechanical equipment cost Implications. In particular, the use of reactors wherein reaction cooling is effected by means of heat exchangers in contact with the reaction medium may be practical in a solution phase process, whereas the susceptibility of such heat exchangers to fouling may rule out such options for a slurry-phase process.

The invention will now be described in more detail, by way of example only, with reference to the following non-limiting examples.

EXAMPLES

The following abbreviations are used in the examples:
PCl chlorophosphine, i.e. R$^1$R$^2$PCl, where R$^1$ and R$^2$ are organyl groups
n-Bu normal-butyl
n-Hex normal hexyl
Et ethyl
Ph phenyl
PNH phosphinoamine, e.g. Ar$_2$PN(R)H, where Ar is an aryl, and R is an organyl group
PNP bis phosphinoamine e.g. Ar$_2$PN(R)PAr$_2$, where Ar is an aryl, and R is an organyl group
DCM dichloromethane
THF tetrahydrofuran
DMF dimethylformamide
TMP 2,2,4-trimethylpentane
MMAO-3A An aluminoxane product General Experimental Conditions for Ligand Synthesis All reactions were carried out under an argon atmosphere using a dual vacuum/nitrogen line and standard Schlenk techniques. Solvents were purified via an M-Braun solvent purification system. All reagents purchased from commercial suppliers were used without further purification. NMR spectra were recorded on a Varian 400 MHz spectrometer using CDCl$_3$. PNP compounds below were prepared by modification of the procedure described in *Synthesis*, 2007, 24, 38863.

Preparation of 7-bromobenzofuran

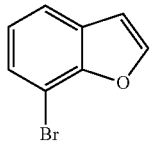

7-bromobenzofuran was prepared as described in Heterocycl. Commun., Vol. 16(4-6), pp. 249-252, 2010 by Klenk. J. et. al.

Preparation of 7-bromobenzothiophene

To a solution of 2-bromothiophenol (12.0 g, 63.4 mmol) in anhydrous DMF was added anhydrous K$_2$CO$_3$ (19.0 g, 137.7 mmol) and bromoacetaldehyde diethyl acetal (12.5 g, 63.4 mmol). The resulting suspension was heated at 95° C. for about 15 hours. After cooling, the reaction mixture was poured into water and the organics were extracted three times with ethyl acetate. The ethyl acetate fraction was washed with 1N NaOH solution and several times with water. The organic phase was dried over MgSO$_4$ and evaporated in vacuo to give S-alkylated bromophenyl acetaldehyde diethyl acetal compound as an oily substance, which was used in the next step without further purification. The oily product was added to a mixture of polyphosphoric acid (60 g) in chlorobenzene (100 ml) and the resulting mixture was heated at ~130° C. overnight. After cooling, chlorobenzene was decanted from the residue. The residue was extracted with toluene. The chlorobenzene and toluene extracts were combined and evaporated in vacuo. The residue was redissolved in diethyl ether and washed with water. The ether phase was dried over MgSO$_4$ and evaporated. The residue was purified over silica column chromatograph, eluting with hexane. The desired 7-bromobenzothiophene was isolated as clear oil.

$^1$H NMR (CDCl$_3$): δ 7.25 (1H, t, J=7.6 Hz), 7.41 (1H, d, J=5.6), 7.46 (2H, m), 7.75 (1H, d, J=8.8 Hz).

Preparation of 1-benzofuran-7-yl magnesium bromide

To magnesium turnings (225 mg, 9.4 mmol) in THF (5 mL) was added 1 iodine crystal and a few drops of 7-bromobenzofuran. A vigorous reaction ensued. The remaining 7-bromobenzofuran (1.8 g, 9.1 mmol) in THF (10 ml) was added dropwise. The reaction mixture was left to reflux by itself. Once the reaction exotherm had dissipated, the reaction mixture was heated under reflux for about 15 minutes to yield the required Grignard reagent.

Preparation of 1-benzothiophen-7-yl magnesium bromide

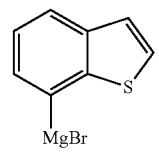

To magnesium turnings (230 mg, 9.6 mmol) in THF (5 mL) was added 1 iodine crystal and a few drops of 7-bromobenzothiophene. A vigorous reaction ensued. The remaining 7-bromobenzothiophene (1.7 g, 8.0 mmol) in THF (10 ml) was added dropwise. The reaction mixture was left to reflux by itself. Once the reaction exotherm had dissipated, the reaction mixture was heated under reflux for about 15 minutes to yield the required Grignard reagent.

Preparation of (1-benzofuran-7-yl)₂phosphinechloride

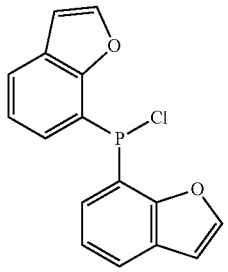 [SMILES: ClP(c1cccc2ccoc12)c1cccc2ccoc12]

The Grignard reagent benzofuryl magnesium bromide (prepared as described from above, separated from excess Mg) (9.1 mmol) was slowly added to an icebath-cooled solution of PCl₃ (0.40 mL, 4.5 mmol) in anhydrous THF (20 ml). After addition was complete, the suspension was stirred at room temperature for a further 1 h after which the reaction was complete as judged by $^{31}$P NMR. The product was used in the next step without Isolation.

$^{31}$P NMR (CDCl₃): δ 61.8 (s), 48.2 (s).

Preparation of (1-benzofuran-7-yl(phenyl)phosphinechlodride

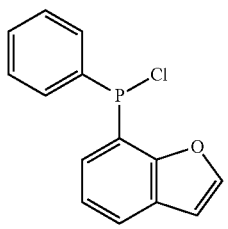 [SMILES: ClP(c1ccccc1)c1cccc2ccoc12]

The same method as described for (1-benzofuran-7-yl)₂ phosphinechloride above was used, except that 1 equivalent of the 1-benzofuran-7-yl magnesium bromide (prepared as described above) was added to PhPCl₂ (instead of PCl₃).

$^{31}$P NMR (CDCl₃): δ 79.4 (s), 67.0 (s).

Preparation of (5-dibenzofuran-4-yl)(phenyl)phosphinechloride

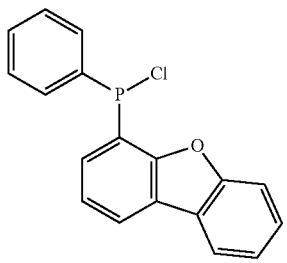 [SMILES: ClP(c1ccccc1)c1cccc2c1oc1ccccc12]

To a THF solution (20 ml) of dibenzofuran (3.0 g, 17.8 mmol) was added n-BuLi (8.6 m, 21.4 mmol) dropwise at −78° C. The reaction was allowed to slowly warm up to room temperature and left to stir overnight. The mixture was slowly added to Et₂NPPhCl (3.2 g, 13.9 mmol) (prepared from Et₂NH (1.01 g, 13.9 mmol), Et₃N (2.79 g, 27.6 mmol), and PhPCl₂ (3.0 g, 13.9 mmol) at −78° C. in 20 ml of THF.) The THF solvent was removed in vacuo followed by addition of Et₂O and filtration of the solids. The supernatant ether solution was then treated with HCl in ether to give the desired PCl upon removal of the solvent.

$^{31}$P NMR (CDCl₃): δ 71.0 (s).

Preparation of (1-benzothiophen-7-yl)(phenyl)phosphinechloride

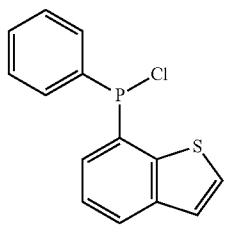 [SMILES: ClP(c1ccccc1)c1cccc2ccsc12]

The same method as described for (1-benzofuran-7-yl)₂ phosphinechloride above was used, except that 1 equivalent of the 1-benzothiophen-7-yl magnesium bromide was added to PhPCl₂ (instead of PCl₃).

$^{31}$P NMR (CDCl₃): δ 76.8 (s), 65.8 (s).

Preparation of 5-chlorodibenzophosphole

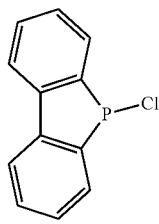 [SMILES: Clp1c2ccccc2c2ccccc21]

To a cooled (0° C.) solution of the 2,2′-dibromobiphenyl (4 g, 12.8 mmol) in Et₂O (40 ml), n-BuLi (11.3 ml, 28.2 mmol, 2.5 M solution in Et₂O) was added drop-wise. After complete addition the cooling bath was removed and the yellow solution was stirred at room temperature for 1 h. The solution was then frozen with liquid nitrogen (−196° C.). Subsequently, PCl₃ (6.7 ml, 76.9 mmol) was added and the reaction mixture allowed to warm to −110° C. When the reaction mixture began to thaw, it was quickly homogenized with swirling. The homogenous solution was allowed to warm to room temperature with stirring and a white precipitate formed. The reaction mixture was evaporated to dryness, and the residue re-dissolved in Et₂O and filtered through a celite bed to give the product.

$^{31}$P NMR (CDCl₃): δ 68.341 (br. s).

Preparation of 2-hydroxy-3-iodobenzaldehyde (3-iodosalicylaldehyde)

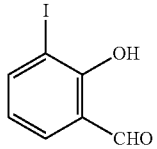

Triethylamine (25.2 ml, 182 mmol) was added to a stirred mixture of anhydrous magnesium chloride (17.3 g, 182 mmol) and paraformaldehyde (8.19 g, 272 mmol) in anhydrous THF (200 ml). 2-Iodophenol (20.0 g, 90.90 mmol) was added dropwise and the reaction was refluxed for 5 h. The reaction was cooled to room temperature and aqueous 1N HCl (100 ml) was added. The aqueous phase was extracted with ether (3×100 ml). The combined dark orange ether phase was filtered through a short silica column to give a pale yellow ether solution. Removal of the volatiles in vacuo afforded a bright yellow solid of the aldehyde product sufficiently pure for further synthetic use. $^1$H NMR δ (CDCl$_3$): 11.82 (s, 1H, OH), 9.77 (s, 1H, CHO), 8.01 (d, 1H, J=8.0 Hz, aromatics), 7.56 (d, 1H, J=8.0 Hz, aromatics), 6.86 (t, 1H, J=7.6 Hz, aromatics).

Preparation of 8-iodo-chromen-2-one

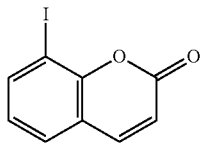 [SMILES: O=c1ccc2cccc(I)c2o1]

To a stirred solution of 3-iodosalicylaldehyde (15.0 g, 60.5 mmol) in acetic anhydride (50 ml) was added potassium acetate (3.7 g, 24.2 mmol). The mixture was refluxed for 5 h. The reaction mixture was cooled to room temperature and diluted with ethyl acetate. The organic layer was washed with saturated aqueous NaCl, dried over magnesium sulfate and concentrated in vacuo. The residue was purified by silica chromatography, eluting with hexane:ethyl acetate (10:1) to give 8-iodo-chromen-2-one as a cream white solid. $^1$H NMR δ (CDCl$_3$): 7.98 (dd, 1H, J=8.0, 1.6 Hz), 7.64 (d, 1H, J=9 Hz, aromatics), 48 (dd, 1H, J=7.6, 1.6 Hz, aromatics), 7.06 (t, 1H, J=7.6 Hz, aromatics).

Preparation of (chromen-2-on-8-yl)(phenyl)phosphinechloride

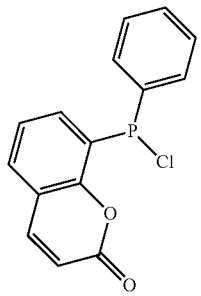 [SMILES: O=c1ccc2cccc(P(Cl)c3ccccc3)c2o1]

To a stirred solution of 8-iodo-chromen-2-one (1.0 g, 3.68 mmol) in anhydrous THF (10 mL) at −78° C. was added iPrMgCl.LiCl (4.2 ml, 5.5 mmol, 1.3 M in THF) solution. The reaction mixture was immediately warmed to 0° C. and stirred for a further 30 min. The reaction mixture was slowly added to a solution of PhPCl$_2$ (0.66 g, 3.68 mmol) in anhydrous THF (15 ml) at −78° C. After addition was complete, the suspension was immediately allowed to warm to room temperature and then stirred at room temperature for a further 20 min after which the reaction was complete as judged by $^{31}$P NMR (CDCl$_3$): δ 71.12 (s).

Preparation of (2-methoxyphenyl)(phenyl)phosphinechloride

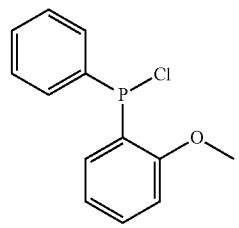 [SMILES: COc1ccccc1P(Cl)c1ccccc1]

1-Bromo-2-methoxybenzene (2.0 g, 10.7 mmol) was added to a mixture of magnesium turnings (0.3 g, 12.8 mmol) in anhydrous THF (20 ml). A vigorous reaction ensued. Stirring was continued at room temperature. Once the reaction exotherm had dissipated, the reaction mixture was used for the next step as described below:

The Grignard reagent (from above, separated from excess Mg) was incrementally added to a solution of PhPCl$_2$ (1.5 mL, 10.7 mmol) in anhydrous THF (30 ml) at −78° C. After addition was complete, the suspension was stirred at room temperature for a further 15 min after which the reaction was complete as Judged by $^{31}$P NMR. The product was used in the next step without isolation.

$^{31}$P NMR (CDCl$_3$): δ 77.07 (s); 68.80 (s).

Preparation of (2-thiomethoxyphenyl)$_2$phosphinechloride

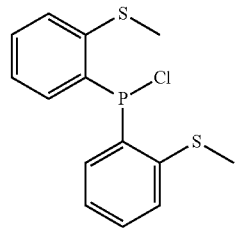 [SMILES: CSc1ccccc1P(Cl)c1ccccc1SC]

1-Bromo-2-thiomethoxybenzene (1.3 mL, 10.7 mmol) was added to a mixture of magnesium turnings (0.28 g, 11.7 mmol) in anhydrous THF (20 ml). A vigorous reaction ensued. Stirring was continued at room temperature until all the magnesium had dissolved. Once the reaction exotherm had dissipated, the reaction mixture was used for the next step as described below:

The Grignard reagent (from above, separated from excess Mg) was incrementally added to a solution of PCl$_3$ (0.43 mL, 5.4 mmol) in anhydrous THF (30 ml) at −78° C. After addition was complete, the suspension was stirred at room temperature for a further 15 min after which the reaction was complete as judged by $^{31}$P NMR. The product was used in the next step without isolation.

$^{31}$P NMR (CDCl$_3$): δ 55.77 (s); 49.40 (s).

Preparation of (1-benzofuran-7-yl)$_2$PN(n-Hex)P(phenyl)$_2$

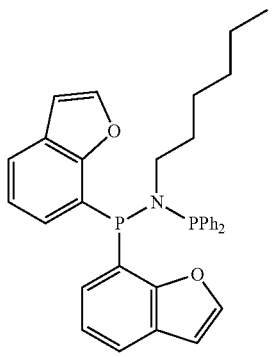

PNH formation: n-Hexylamine (0.95 mL, 7.2 mmol) and Et$_3$N (1.0 mL, 7.2 mmol) were added to the crude (1-Benzofuran-7-yl)$_2$phosphinechloride (1.1 g, 3.6 mmol) [prepared as described above] in diethyl ether (30 ml). The reaction mixture was stirred at room temperature until complete formation of the PNH intermediate as judged by $^{31}$P NMR analysis. The volatiles were removed in vacuo. Ether (50 ml) was added and the resultant mixture filtered to give the ether solution of the desired PNH product in reasonable purity [by $^{31}$P NMR analysis]. The solvent was evaporated to give the PNH compound, (1-benzofuran-7-yl)$_2$ PN(n-Hex)H.

$^{31}$P NMR (CDCl$_3$): δ 22.5 (s).

PNP formation: The PNH molecule described above (0.90 g, 2.4 mmol) was re-dissolved in DCM (10 ml). Et$_3$N (0.5 g, 4.9 mmol) was added, followed by incremental addition of Ph$_2$PCl (1.1 g, 4.9 mmol) at room temperature. After complete conversion of the PNH (judged by $^{31}$P NMR analysis) to the PNP, the volatiles were removed in vacuo. Ether (100 ml) was added and the resultant mixture was filtered through a short activated alumina column. Filtration was repeated until a pure compound was obtained. The solvent was evaporated to give the desired PNP product.

$^{31}$P NMR (CDCl$_3$): δ 63.0 (d, J=49.3 Hz), 40.3 (d, J=49.3 Hz).

Preparation of (1-benzofuran-7-yl)(phenyl)PN(n-Hex)P(phenyl)$_2$

PNH formation: (1-benzofuran-7-yl)(phenyl)PN(n-Hex)H was prepared as described above for (1-benzofuran-7-yl)$_2$PN(n-Hex)H except that (1-benzofuran-7-yl)(phenyl)phosphinechloride was used instead of (1-benzofuran-7-yl)$_2$phosphinechloride.

PNP formation: The PNP compound was prepared from the reaction of (1-benzofuran-7-yl)(phenyl)PN(n-Hex)H (1.2 g, 4.0 mmol), Et$_3$N (0.8 g, 8.1 mmol), and Ph$_2$PCl (1.8 g, 4.0 mmol) following the typical procedure described for (1-benzofuran-7-yl)$_2$PN(n-Hex)P(phenyl)$_2$ above.

$^{31}$P NMR (CDCl$_3$): δ 62.9 (d, J=37.6 Hz), 50.5 (d, J=37.6 Hz).

Preparation of (5-dibenzofuran-4-yl)(phenyl)PN(n-Bu)P(phenyl)$_2$

PNH formation: (5-dibenzofuran-4-yl)(phenyl)PN(n-Bu)H was prepared using the same method described for (1-benzofuran-7-yl)$_2$PN(n-Hex)H except that (5-dibenzofuran-4-yl)(phenyl)PCl was used instead of (1-benzofuran-7-yl)$_2$PCl and n-Butylamine was used instead of n-Hexylamine.

$^{31}$P NMR (CDCl$_3$): δ 32.8(s).

PNP formation: The PNP compound was prepared from the reaction of (5-dibenzofuran-4-yl)(phenyl)PN(n-Bu)H (0.5 g, 1.50 mmol), Et$_3$N (0.45 g, 4.53 mmol), and Ph$_2$PCl (0.33 g, 1.50 mmol) using the method described for (1-benzofuran-7-yl)$_2$PN (n-Hex)P(phenyl)$_2$.

$^{31}$P NMR (CDCl$_3$): δ 62.8 (d, J=36.1 Hz), 49.7 (d, J=36.1 Hz).

Preparation of (1-benzofuran-7-yl(phenyl)PN(n-Bu)P(furan-2-yl)$_2$

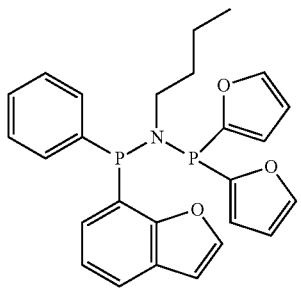 [SMILES: CCCCN(P(c1ccco1)c1ccco1)P(c1ccccc1)c1cccc2ccoc12]

PNH formation: (1-benzofuran-7-yl)(phenyl)PN(n-Bu)H was prepared as described above for (1-benzofuran-7-yl)(phenyl)PN(n-Hex)H except that n-Butylamine was used instead of n-Hexylamine.

PNP formation: The PNP compound was prepared from the reaction of (1-benzofuran-7-yl)(phenyl)PN(n-Bu)H (1.1 g, 3.70 mmol), Et$_3$N (1.1 g, 11.1 mmol), and (furan-2-yl)$_2$PCl (0.74 g, 5.55 mmol) following the typical procedure described above for (1-benzofuran-7-yl)$_2$PN(n-Hex)P(phenyl)$_2$.

$^{31}$P NMR (CDCl$_3$): δ 53.3 (d, J=75.5 Hz), 9.9 (d, J=75.7 Hz).

Preparation of (1-benzofuran-7-yl(phenyl)PN(n-Bu)(dibenzophosphol-5-yl)

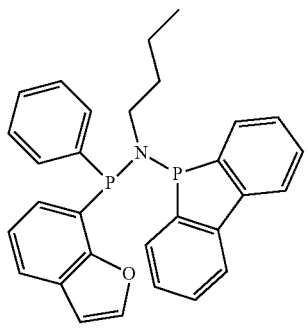 [SMILES: CCCCN(P(c1ccccc1)c1cccc2ccoc12)p1c2ccccc2c2ccccc21]

PNH formation: n-butyl amine (0.98 ml, 10 mmol) and Et$_3$N (1.40 ml, 10 mmol) were added to the crude 5-chlorodibenzophosphole (1.3 g, 6 mmol) [prepared as described above] in diethyl ether (30 ml). The reaction mixture was stirred at room temperature until complete formation of the PNH intermediate as judged by $^{31}$P NMR analysis. The volatiles were removed in vacuo. Ether (50 ml) was added and the resultant mixture filtered to give the ether solution of the desired PNH product in reasonable purity [(by $^{31}$P NMR analysis]. The solvent was removed in vacuo to give the PNH compound, (dibenzophosphol-5-yl)N(n-butyl)H.

$^{31}$P NMR (CDCl$_3$): 37.2 (s).

PNP formation: The PNP compound was prepared from the reaction of (dibenzophosphol-5-yl)-N(n-butyl)H (1.5 g, 5.9 mmol), Et$_3$N (1.1 ml, 8.3 mmol), and (1-benzofuran-7-yl)(phenyl)-phosphinechloride (1.8 g, 7.1 mmol) following the typical procedure described for the preparation of (1-benzofuran-7-yl)$_2$PN(n-Hex)P(phenyl)$_2$ above.

$^{31}$P NMR (CDCl$_3$): δ 55.85 (d, J=93.5 Hz), 53.92 (d, J=94.2 Hz).

Preparation of (1-benzothiophen-7-yl)(phenyl)PN(n-Hex)P(phenyl)$_2$

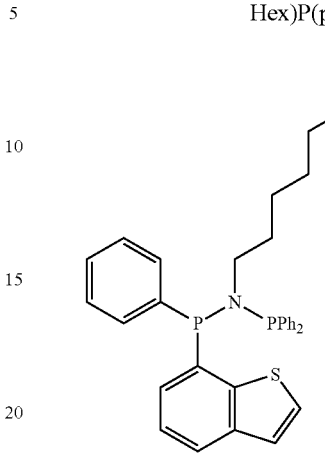

The same method was used as described in the procedure for (1-benzofuran-7-yl)$_2$PN(n-Hex)P(phenyl)$_2$, except that (1-benzothiophen-7-yl)(phenyl)phosphinechloride was used instead of (1-benzofuran-7-yl)$_2$phosphinechloride.

PNH: (1-benzothiophen-7-yl)(phenyl)PN(n-Hex)H, $^{31}$P NMR (CDCl$_3$)=37.2 (s). PNP: $^{31}$P NMR (CDCl$_3$): δ 61.4 (d, J=34.6 Hz), 57.8 (d, J=36.1 Hz).

Preparation of (quinol-8-yl)(phenyl)PN(n-Bu)P(phenyl)$_2$

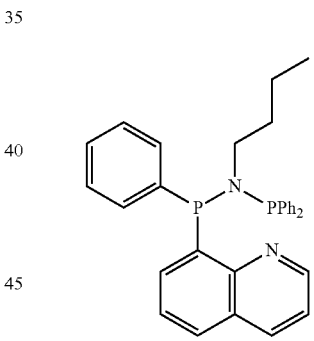

PNPCl formation: To a stirred solution of excess n-butylamine (22.4 ml, 227.1 mmol) in diethyl ether (100 ml) at 0° C. was added Ph$_2$PCl (4.2 ml, 22.7 mmol) dropwise. After complete addition of Ph$_2$PCl, triethylamine (6.3 ml, 45.3 mmol) was added and the reaction was left to warm up to room temperature. The reaction mixture was filtered through a short alumina column and the volatiles (solvent and unreacted amine) were removed in vacuo to give the desired PNH, Ph$_2$PN(nBu)H, which was used in the next step (below) without further purification.

$^{31}$P NMR (CDCl$_3$): δ 40.91 (s).

The PNH compound (6.4 g, 24.9 mmol) obtained above was added slowly to a stirred solution of PhPCl$_2$ (3.3 ml, 24.3 mmol) and triethylamine (6.8 ml, 48.9 mmol) in diethyl ether (150 ml) at 0° C. After complete addition, the reaction mixture was filtered through Celite and the volatiles removed in vacuo. A yellow, sticky oil was isolated and the oil was extracted with pentane. The pentane extract was filtered and evaporated in vacuo to give a thick clear oil of Ph₂PN(nBu)P(Cl)Ph, which solidified upon standing.

³¹P NMR (CDCl₃): δ 139.24 (d, J=154.64 Hz), 65.34 (d, J=154.64 Hz).

PNP formation: To a stirred solution of 8-bromoquinoline (2.0 g, 9.6 mmol) in anhydrous THF (20 ml) at −78° C. was added n-butyllithium (4.7 ml, 2.5 M in hexane, 12.2 mmol). The solution was stirred at −78° C. for 2 hours. The resulting 8-quinolyllithium was added in portions to a stirred solution of Ph₂PN(nBu)PPhCl (1.75 g, 4.38 mmol) in anhydrous THF (10 mL) at −78° C. until complete consumption of PNPCl (as shown by ³¹PNMR). The reaction mixture was left to warm to room temperature and the THF was removed in vacuo. The resultant yellow paste was slurried in diethyl ether (80 ml) and the mixture was filtered through a short alumina column. The filtrate was evaporated in vacuo to afford a yellow solid, which washed with pentane to give the desired PNP, (quinol-8-yl)(phenyl)PN(n-Bu)P(phenyl)₂, as a yellow powder.

³¹P NMR (CDCl₃): δ 60.48 (bs), 54.12 (bs).

Preparation of (chromen-2-one-8-yl(phenyl)PN(nBu)P(phenyl)₂

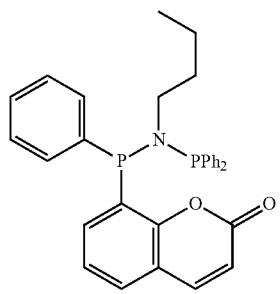

PNH formation: The synthesis of Ph₂PN(nBu)H has been described above for the synthesis of Ph₂N(nBu)PPhCl.

PNP formation: The PNH, Ph₂PN(nBu)H molecule (0.49 g, 1.73 mmol) was dissolved in DCM (10 ml). Et₃N (0.35 g, 3.46 mmol) was added, followed by addition of (chromen-2-on-8-yl)(phenyl)PCl (500 mg, 1.73 mmol) at room temperature. After complete conversion of PCl (as judged by ³¹P NMR analysis) to the PNP, the volatiles were removed in vacuo. Ether (100 ml) was added and the resultant mixture was filtered through a short column of activated alumina to give the desired PNP upon solvent removal. ³¹P NMR (CDCl₃): δ 60.8 (br s), 49.1 (br s).

Preparation of (phenyl)₂PN(n-Bu)P(phenyl)₂

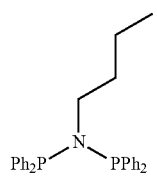

This compound was prepared from the reaction of n-Butylamine (1.0 g, 13.7 mmol), Et₃N (5.54 g, 54.7 mmol), Ph₂PCl (7.59 g, 41.0 mmol), following a procedure described in *Synthesis*, 2007, 24, 3863.

³¹P NMR (CDCl₃): δ 62.5 (s).

Preparation of (2-methoxyphenyl)(phenyl)PN(n-Bu)P(phenyl)₂

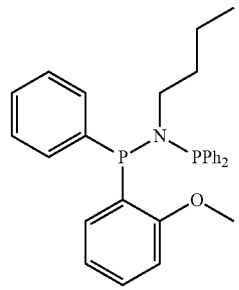

PNH formation: An ethereal solution of n-Butylamine (1.5 g, 20.1 mmol) and Et₃N (2.0 g, 20.1 mmol) at ~0° C. was added to an ethereal solution of (2-methoxyphenyl)(phenyl)PCl (10.0 mmol). A white precipitate formed immediately. The reaction mixture was left to stir for 1 hr followed by filtration of the precipitate and removal of the solvent in vacuo to give (2-methoxyphenyl)(phenyl)PN(n-Bu)H.

³¹P NMR (CDCl₃): δ 34.82 (s).

PNP formation: To a DCM (3 ml) solution of (2-methoxyphenyl)(phenyl)N(Bu)H (2.4 g, 8.5 mmol) and Et₃N (1.4 ml, 10.2 mmol) was added ClPPh₂ (1.58 g, 8.5 mmol). The reaction was left to stir overnight. The solvent was then removed in vacuo and the residue re-slurried in ether (100 ml), followed by filtration of the S solids and removal of the solvent in vacuo to give a clear yellowish oil.

³¹P NMR; δ (CDCl₃): 61.42 (d, J=35.34); 52.28 (d, J=35.99).

Preparation of (2-thiomethoxyphenyl)₂PN(n-Bu)P(phenyl)₂

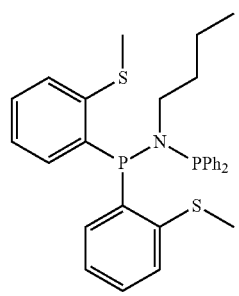

PNH formation: An ethereal solution of n-Butylamine (1.5 ml, 20.1 mmol) and Et₃N (2.0 g, 20.1 mmol) at ~0° C. was added to an ethereal solution of (2-thiomethoxyphenyl)₂PCl (10.0 mmol). A white precipitate formed immediately. The reaction mixture was left to stir for 1 hr followed by filtration of the precipitate and removal of the solvent in vacuo to give (2-thiomethoxyphenyl)₂PN (n-Bu)H.

³¹P NMR (CDCl₃): δ 22.91 (s).

PNP formation: To a DCM (3 ml) solution of (2-thiomethoxyphenyl)₂PN(n-Bu)H (3.0 g, 8.6 mmol) and Et₃N (1.0 ml) was added ClPPh₂ (0.91 mL, 4.9 mmol). The reaction was left to stir overnight. The solvent was then removed in vacuo and the residue re-slurried in ether (100 ml), followed by filtration of the solids and removal of the solvent in vacuo to give a white powder.

$^{31}$P NMR; δ (CDCl$_3$): 56.96 (d, J=29.83 Hz), 44.41 (d, J=29.83 Hz).

Preparation of (1-naphthyl)$_2$PN(n-Bu)P(phenyl)$_2$

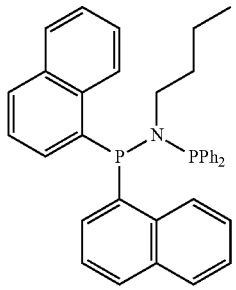

PNH formation: To an ether solution (10 ml) of n-Butylamine (0.35 g, 4.69 mmol) was added ClP(1-naphthyl)$_2$ (0.5 g, 1.56 mmol) and Et$_3$N (0.45 g, 4.70 mmol). The reaction mixture was left to stir for 2 hrs followed by filtration of the solids and removal of the solvent to give the PNH molecule (1-naphthyl)$_2$PN(n-Bu)H.

$^{31}$P NMR (CDCl$_3$): δ 25.6 (a).

PNP formation: The half molecule (1-naphthyl)$_2$PN(n-Bu)H (0.4 g, 1.12) was treated with Et$_3$N (0.34 g, 3.36 mmol) and ClPPh$_2$ (0.49 g, 2.23 mmol) to give the desired PNP, following a procedure described in *Synthesis*, 2007, 24, 3863.

$^{31}$P NMR (CDCl$_3$): δ 63.4 (d, J=79.1 Hz), 48.6 (d, J=79.1 Hz).

Example 1

Ethylene Tetramerisation with (1-benzofuran-7-yl)$_2$PN(n-Hex)P(phenyl)$_2$ at 60° C. and 45 bar A 600 ml stainless steel reactor was heated to 120° C. for 30 minutes under vacuum, backfilled with N$_2$ and then cooled to 60° C. The reactor was charged with 2,2,4-trimethylpentane (TMP) (100 ml), and heated to 60° C. Separately, MMAO-3A (2.4 mmol Al) was added to a mixture of Cr(acac)$_3$ (2.5 µmol) and (1-benzofuran-7-yl)$_2$PN(n-Hex)P(phenyl)$_2$ (2.5 µmol) in cyclohexane (5 ml). This mixture was then transferred to the reactor. The reactor was pressurised with ethylene (45 bar), and stirred (1300 r.p.m.) with a gas entraining stirrer. The temperature in the reactor increased to 62-65° C., at which point the reactor was cooled by means of an internal cooling coil to maintain a constant temperature of 60° C. throughout the run. The reaction pressure was kept constant throughout the run by feeding ethylene on demand, and the consumption of ethylene was monitored via a flow meter. At the conclusion of the run after 12 minutes and 160 g total ethylene uptake (including the ethylene required to pressurise the reactor), the reactor was rapidly cooled to 5° C., and depressurised. A weighed mass of nonane was added as an internal standard, and a small sample was taken for GC-FID analysis. The polymer by-product was collected by filtration, dried overnight and weighed. The selectivity and activity were then calculated from the GC data and polymer mass. The results are shown in Table 1.

Example 2

Ethylene Tetramerisation with (1-benzofuran-7-yl)(phenyl)PN(n-Hex)P(phenyl)$_2$ at 60° C. and 45 bar The procedure of example 1 was followed, except that 1.0 mmol Al as MMAO-3A, 1.0 µmol Cr(acac)$_3$ and the ligand (1-benzofuran-7-yl)(phenyl)PN(n-Hex)P(phenyl)$_2$ (1.0 µmol) was used, and the reaction was terminated after 17 minutes and 150 g ethylene uptake. The results are shown in Table 1.

Example 3

Ethylene Tetramerisation with (5-dibenzofuran-4-yl)(phenyl)PN(n-Bu)P(phenyl)$_2$ at 60° C. and 45 bar The procedure of example 1 was followed, except that 1.0 mmol Al as MMAO-3A, 1.0 µmol Cr(acac)$_3$ and the ligand (5-dibenzofuran-4-yl)(phenyl)PN(n-Bu)P(phenyl)$_2$ was used, and the reaction was terminated after 14 minutes and 150 g ethylene uptake. The results are shown in Table 1.

Example 4

Ethylene Tetramerisation with (1-benzofuran-7-yl)$_2$PN(n-Hex)P(phenyl)$_2$ at 100° C. and 45 bar The procedure of example 1 was followed, except that 200 ml of TMP was used, the reaction temperature was maintained at 100° C. and the reaction was terminated after 14 minutes and 150 g ethylene uptake. The results are shown in Table 1.

Example 5

Ethylene Tetramerisation with (1-benzofuran-7-yl)(phenyl PN(n-Hex)P(phenyl)$_2$ at 100° C. and 45 bar The procedure of example 1 was followed, except the ligand (1-benzofuran-7-yl)(phenyl)PN(n-Hex)P(phenyl)$_2$ was used, 200 ml of TMP was used, the reaction temperature was maintained at 100° C., and the reaction was terminated after 22 minutes and 150 g ethylene uptake. The results are shown in Table 1.

Example 6

Ethylene Tetramerisation with (1-benzofuran-7-yl)(phenyl)PN(n-Bu)(furan-2-yl)$_2$ at 100° C. and 45 bar The procedure of example 1 was followed, except that the ligand (1-benzofuran-7-yl)(phenyl)PN(n-Bu)P(furan-2-yl)$_2$ was used, 200 ml of TMP was used, the reaction temperature was maintained at 100° C., and the reaction was terminated after 65 minutes and 150 g ethylene uptake. The results are shown in Table 1.

Example 7

Ethylene Tetramerisation with (1-benzofuran-7-yl)(phenyl)PN(n-Bu)(dibenzophosphol-5-yl) at 100° C. and 45 bar The procedure of example 1 was followed, except that the ligand (1-benzofuran-7-yl)(phenyl)PN(n-Bu)(dibenzophosphol-5-yl) was used, 200 ml of TMP was used, the reaction temperature was maintained at 100° C. and the reaction was terminated after 42 minutes and 150 g ethylene uptake. The results are shown in Table 1.

Example 8

Ethylene Tetramerisation with (1-benzothiophen-7-yl)(phenyl)PN(n-Hex)P(phenyl)$_2$ at 60° C. and 45 bar The procedure of example 1 was followed, except that the ligand (1-benzothiophen-7-yl)(phenyl)PN(n-Hex)P(phenyl)$_2$ was used, and the reaction was terminated after 16 minutes and 160 g ethylene uptake. The results are shown in Table 1.

Example 9

Ethylene Tetramerisation with (1-benzothiophen-7-yl)(phenyl)PN(n-Hex)P(phenyl)$_2$ at 100° C. and 45 bar The procedure of example 1 was followed, except that the ligand (1-benzothiophen-7-yl)(phenyl)PN(n-Hex)P(phenyl)$_2$ was used, 200 ml of TMP was used, the reaction temperature was maintained at 100° C., and the reaction was terminated after 33 minutes and 150 g ethylene uptake. The results are shown in Table 1.

Example 10

Ethylene Tetramerisation with (1-benzothiophen-7-yl)(phenyl)PN(n-Hex)P(phenyl)$_2$ at 90° C. and 60 bar The procedure of example 1 was followed, except that the ligand (1-benzothiophen-7-yl)(phenyl)PN(n-Hex)P(phenyl)$_2$ was used, 200 ml of TMP was used, the reaction temperature was maintained at 90° C., the ethylene pressure was maintained at 60 bar, and the reaction was terminated after 26 minutes and 150 g ethylene uptake. The results are shown in Table 1.

Example 11

Ethylene Tetramerisation with (quinol-8-yl)(phenyl)PN(n-Bu)P(phenyl)$_2$ at 60° C. and 45 bar The procedure of example 1 was followed, except that the ligand (quinol-8-yl)(phenyl)PN(n-Bu)P(phenyl)$_2$ was used and the reaction was terminated after 30 minutes and 56 g ethylene uptake. The results are shown in Table 1.

Example 12

Ethylene Tetramerisation with (chromen-2-on-8-yl)(phenyl)PN(n-Bu)P(phenyl)$_2$ at 60° C. and 45 bar The procedure of example 1 was followed, except that the ligand (chromen-2-on-8-yl)(phenyl)PN(n-Bu)P(phenyl)$_2$ (2.5 µmol) was used and the reaction was terminated after 30 minutes and 60 g ethylene uptake. The results are shown in Table 1.

Example 13

Ethylene Tetramerisation with (5-dibenzofuran-4-yl)(phenyl)PN(n-Bu)P(phenyl)$_2$ at 60° C. and 45 bar A 600 ml stainless steel reactor was heated to 120° C. for 30 minutes under vacuum, backfilled with N$_2$ and then cooled to 60° C. The reactor was charged with methylcyclohexane (MCH) (200 ml), triethylaluminium (465 µmol) and diethylzinc (140 µmol) and heated to 60° C. Separately, [N(C$_{18}$H$_{37}$)$_2$MeH][B(C$_6$F$_5$)$_4$] (1.5 µmol) in cyclohexane was added to a mixture of Cr(2-ethylhexanoate)$_3$ (1.25 µmol) and (5-dibenzofuran-4-yl)(phenyl)PN(n-Bu)P(phenyl)$_2$ (1.5 µmol) in MCH. The resulting mixture was stirred for 30 seconds after which triethylaluminium (75 µmol) was added and this mixture was then transferred to the reactor. The reactor was pressurised with ethylene (45 bar), and stirred (1300 r.p.m.) with a gas entraining stirrer. The temperature in the reactor was maintained at 60° C. throughout the run by means of an internal cooling coil and the reaction pressure was kept constant throughout the run by feeding ethylene on demand. The consumption of ethylene was monitored via a flow meter. At the conclusion of the run after 19 minutes and 150 g total ethylene uptake (including the ethylene required to pressurise the reactor), the reactor was rapidly cooled to 5° C., and depressurised. A weighed mass of nonane was added as an internal standard, and a small sample was taken for GC-FID analysis. The polymer by-product was collected by filtration, dried overnight and weighed. The selectivity and activity were then calculated from the GC data and polymer mass. The results are shown in Table 1.

Example 14

Ethylene Tetramerisation with (5-dibenzofuran-4-yl)(phenyl)PN(n-Bu)P(phenyl)$_2$ at 60° C. and 45 bar A 600 ml stainless steel reactor was heated to 120° C. for 30 minutes under vacuum, backfilled with N$_2$ and then cooled to 60° C. The reactor was charged with methylcyclohexane (MCH) (180 m) and trimethylaluminum (750 µmol) and heated to 60° C. Separately, Witco MAO/SO$_2$ (product code TA 02 794) (0.25 g) was added to a mixture of Cr(acac)$_3$ (2.5 µmol) and (5-dibenzofuran-4-yl)(phenyl)PN(n-Bu)P(phenyl)$_2$ (2.5 µmol) in MCH (20 ml), and the resulting slurry was stirred for 1 minute. This slurry was then transferred to the reactor after which the reactor was pressurised with ethylene (45 bar), and stirred (1300 r.p.m.) with a gas entraining stirrer. The temperature in the reactor was maintained at 60° C. throughout the run by means of an internal cooling coil and the reaction pressure was kept constant by feeding ethylene on demand. Ethylene consumption was monitored via a flow meter. At the conclusion of the run after 30 minutes and 85 g total ethylene uptake (including the ethylene required to pressurise the reactor), the reactor was rapidly cooled to 5° C., and depressurised. A weighed mass of nonane was added as an internal standard, and a small sample was taken for GC-FID analysis. The polymer by-product was collected by filtration, dried overnight and weighed. The selectivity and activity were then calculated from the GC data and polymer mass. The results are shown in Table 1.

Comparative Example 1

Ethylene Tetramerisation with (phenyl)$_2$PN(n-Bu)P(phenyl)$_2$ at 60° C. and 45 bar The procedure of example 1 was followed, except that the ligand Ph$_2$PN(n-Bu)PPh$_2$ was used, and the reaction was terminated after 46 minutes and 160 g ethylene uptake (including the ethylene required to pressurise the reactor). The results are shown in Table 1.

Comparative Example 2

Ethylene Tetramerisation with (phenyl)$_2$PN(n-Bu)P(Phenyl)$_2$ at 100° C. and 45 bar The procedure of example 1 was followed, except that the ligand Ph$_2$PN(n-Bu)PPh$_2$ was used, 200 ml of TMP was used, the reaction temperature was maintained at 100° C., and the reaction was terminated after 30 minutes and 87 g ethylene uptake (including the ethylene required to pressurise the reactor). The results are shown in Table 1.

Comparative Example 3

Ethylene Tetramerisation with (2-methoxyphenyl)(phenyl)PN(n-Bu)P(phenyl)$_2$ at 60° C. and 45 bar The procedure of example 1 was followed, except that ligand (2-methoxyphenyl)(phenyl)PN(n-Bu)P(phenyl)$_2$ was used and the reaction was terminated after 16.2 minutes and 160 g ethylene uptake. The results are shown in Table 1.

Comparative Example 4

Ethylene Tetramerisation with (2-methoxyphenyl)(phenyl)PN(n-Bu)P(phenyl)$_2$ at 100° C. and 45 bar The procedure of example 1 was followed, except that ligand (2-methoxyphenyl)(phenyl)PN(n-Bu)P(phenyl)$_2$ was used, 200 ml of methylcyclohexane was used, the reaction temperature was maintained at 100° C., and the reaction was terminated after 8 minutes and 150 g ethylene uptake. The results are shown in Table 1.

Comparative Example 5

Ethylene Tetramerisation with (2-thiomethoxyphenyl)$_2$PN(n-Bu)P(phenyl)$_2$ at 100° C. and 45 bar The procedure of example 1 was followed, except that ligand (2-thiomethoxyphenyl)$_2$PN(n-Bu)P(phenyl)$_2$ was used, 200 m of TMP was used, the reaction temperature was maintained at 100° C., and the reaction was terminated after 30 minutes and 50.8 g ethylene uptake. The results are shown in Table 1.

Comparative Example 6

Ethylene Tetramerisation with (1-napthyl)$_2$PN(n-Bu)P(phenyl)$_2$ at 100° C. and 45 bar The procedure of example 1 was followed, except that ligand (1-napthyl)$_2$PN(n-Bu)P(phenyl)$_2$ was used, 200 ml of TMP was used, the reaction temperature was maintained at 100° C., and the reaction was terminated after only 30 minutes and 46.1 g ethylene uptake (including the ethylene required to pressurise the reactor). The results are shown in Table 1.

TABLE 1

| Example | Ligand | Temp (° C.), Press. (bar) | Activity (×10$^6$ g/gCr/h) | 1-Hexene selectivity (mass %) | C6 cyclics selectivity (mass %) | 1-Octene setectivity (mass %) | C10-C30 selectivity (mass %) | Polymer selectivity (mass %) | 1-Octene:1-Hexene ratio (g/g) |
|---|---|---|---|---|---|---|---|---|---|
| 1 | (1-benzofuran-7-yl)$_2$PN(n-Hex)P(phenyl)$_2$ | 60, 45 | 4.9 | 26.7 | 4.2 | 58.8 | 8.6 | 0.45 | 2.20 |
| 2 | (1-benzofuran-7-yl)(phenyl)PN(n-Hex)P(phenyl)$_2$ | 60, 45 | 6.5 | 21.7 | 5.6 | 63.8 | 6.7 | 0.31 | 2.94 |
| 3 | (5-dibenzofuran-4-yl)(phenyl)PN(n-Bu)P(phenyl)$_2$ | 60, 45 | 8.0 | 20.3 | 4.0 | 66.2 | 8.0 | 0.20 | 3.27 |
| 4 | (1-benzofuran-7-yl)$_2$PN(n-Hex)P(phenyl)$_2$ | 100, 45 | 3.7 | 63.0 | 2.0 | 27.7 | 6.0 | 0.56 | 0.44 |
| 5 | (1-benzofuran-7-yl)(phenyl)PN(n-Hex)P(phenyl)$_2$ | 100, 45 | 2.3 | 55.6 | 3.0 | 33.1 | 6.8 | 0.63 | 0.59 |
| 6 | (1-benzofuran-7-yl)(phenyl)PN(n-Bu)P(furan-2-yl)$_2$ | 100, 45 | 0.79 | 49.3 | 4.4 | 36.9 | 6.8 | 0.85 | 0.75 |
| 7 | (1-benzofuran-7-yl)(phenyl)PN(n-Bu)(dibenzophosphol-5-yl) | 100, 45 | 1.1 | 43.3 | 1.9 | 44.2 | 7.5 | 1.51 | 1.02 |
| 8 | (1-benzothiophen-7-yl)(phenyl)PN(n-Hex)P(phenyl)$_2$ | 60, 45 | 3.0 | 47.0 | 7.7 | 37.3 | 6.8 | 0.40 | 0.79 |
| 9 | (1-benzothiophen-7-yl)(phenyl)PN(n-Hex)P(phenyl)$_2$ | 100, 45 | 1.5 | 75.7 | 2.1 | 13.7 | 6.3 | 1.72 | 0.18 |
| 10 | (1-benzothiophen-7-yl)(phenyl)PN(n-Hex)P(phenyl)$_2$ | 90, 60 | 1.5 | 69.6 | 3.4 | 21.2 | 4.1 | 1.35 | 0.30 |

TABLE 1-continued

| Example | Ligand | Temp (° C.), Press. (bar) | Activity (×10⁶ g/gCr/h) | 1-Hexene selectivity (mass %) | C6 cyclics selectivity (mass %) | 1-Octene selectivity (mass %) | C10-C30 selectivity (mass %) | Polymer selectivity (mass %) | 1-Octene:1-Hexene ratio (g/g) |
|---|---|---|---|---|---|---|---|---|---|
| 11 | (quinol-8-yl)(phenyl)PN(n-Bu)P(phenyl)₂ | 60, 45 | 0.12 | 30.1 | 6.4 | 44.5 | 2.5 | 12.5 | 1.47 |
| 12 | (chromen-2-on-8-yl)(phenyl)PN(n-Bu)P(phenyl)₂ | 60, 45 | 0.34 | 19.2 | 9.2 | 43.4 | 11.7 | 11.4 | 1.46 |
| 13 | (5-dibenzofuran-4-yl)(phenyl)PN(n-Bu)P(phenyl)₂ | 60, 45 | 3.7 | 24.2 | 4.9 | 63.3 | 6.0 | 0.16 | 2.61 |
| 14 | (5-dibenzofuran-4-yl)(phenyl)PN(n-Bu)P(phenyl)₂ | 60, 45 | 0.34 | 38.9 | 3.4 | 38.9 | 5.5 | 12.4 | 1.00 |
| Comp 1 | (phenyl)₂P N(n-Bu)P(phenyl)₂ | 60, 45 | 1.2 | 6.5 | 9.0 | 59.7 | 19.2 | 1.7 | 9.18 |
| Comp 2 | (phenyl)₂P N(n-Bu)P(phenyl)₂ | 100, 45 | 0.51 | 25.2 | 6.9 | 54.2 | 8.0 | 3.4 | 2.15 |
| Comp 3 | (2-methoxyphenyl)(phenyl)P N(n-Bu)P(phenyl)₂ | 60, 45 | 4.1 | 55.5 | 2.2 | 24.4 | 16.5 | 0.4 | 0.43 |
| Comp 4 | (2-methoxyphenyl)(phenyl)P N(n-Bu)P(phenyl)₂ | 100, 45 | 6.8 | 78.5 | 0.5 | 6.2 | 12.8 | 0.3 | 0.08 |
| Comp 5 | (2-thiomethoxyphenyl)₂PN(n-Bu)P(phenyl)₂ | 100, 45 | 0.021 | 36.4 | 0 | 1.1 | 1.6 | 27.7 | 0.03 |
| Comp 6 | (1-napthyl)₂PN(n-Bu)PPh₂ | 100, 45 | 0.073 | 17.2 | 1.2 | 20.3 | 7.3 | 52.7 | 1.18 |

The invention claimed is:

1. A process for the oligomerisation of ethylene to predominantly 1-hexene or 1-octene or mixtures of 1-hexene and 1-octene, the process including contacting ethylene with a catalyst under ethylene oligomerisation conditions, said catalyst comprising:
   i) a source of chromium;
   ii) a ligating compound of the formula

wherein $P^1$ and $P^2$ are phosphorus atoms;
   X is a linking group between $P^1$ and $P^2$; and
   $R^1$ to $R^4$ are independently a hydrocarbyl group, an organoheteryl group or a heterohydrocarbyl group, wherein at least one of $R^1$, $R^2$, $R^3$, and $R^4$ includes an optionally substituted fused cyclic structure including at least two rings, the optionally substituted fused cyclic structure including a 5- to 7-membered aromatic first ring bonded to the respective phosphorus atom, the aromatic first ring being fused to a 4- to 8-membered heterocyclic second ring, the heterocyclic second ring including a heteroatom, the heteroatom being separated from the respective phosphorous atom by two ring atoms along the shortest path; and
   iii) optionally a catalyst activator or combination of catalyst activators.

2. The process of claim 1, wherein the optionally substituted aromatic first ring bonded to the respective phosphorus atom is a 6 membered aromatic ring.

3. A process for the oligomerisation of ethylene to predominantly 1-hexene or 1-octene or mixtures of 1-hexene and 1-octene, the process including contacting ethylene with a catalyst under ethylene oligomerisation conditions, said catalyst comprising:
   i) a source of chromium;
   ii) a ligating compound of the formula

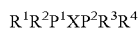

wherein $P^1$ and $P^2$ are phosphorus atoms;
   X is a linking group between $P^1$ and $P^2$; and
   $R^1$ to $R^4$ are independently a hydrocarbyl group, an organoheteryl group or a heterohydrocarbyl group, wherein at least one of $R^1$, $R^2$, $R^3$, and $R^4$ can be represented as Z, where Z includes a fused bicyclic structure including an optionally substituted six-membered aromatic ring fused to an optionally substituted 4- to 8-membered heterocyclic second ring, and which can be represented as:

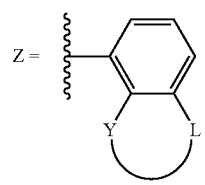

such that Y=O, S, P, N or $NR^5$, where $R^5$ includes hydrogen, halogen, hydrocarbyl, organoheteryl, heterohydrocarbyl or polar groups; and
   L is a linking group between Y and the six-membered aromatic ring; and
   iii) optionally a catalyst activator or combination of catalyst activators.

4. The process of claim 3, wherein L is selected such that Z is an optionally substituted fused bicyclic heteroaryl group incorporating Y as a ring atom of this bicyclic heteroaryl group, where the ring including Y is a 5- or 6-membered ring.

5. The process of claim 3, wherein L is selected from the group comprising a hydrocarbylene group, —N═N— and —$CR^7$═N—, where $R^7$ is a hydrogen, hydrocarbyl or heterohydrocarbyl group.

6. The process of claim 3, wherein L is selected such that Z is an optionally substituted fused bicyclic heteroaryl group including further fused ring structures to form a fused polycyclic structure with more than two rings.

7. The process of claim 3, wherein Z is selected from the group consisting of optionally substituted 1-benzofuran-7-yl, 5-dibenzofuran-4-yl, 1-benzothiophen-7-yl, quinol-8-yl, indol-7-yl and 8-benzophosphabenzene.

8. The process of claim 3, wherein Z is an optionally substituted 1-benzofuran-7-yl group, an optionally substituted 1-benzothiophen-7-yl group or an optionally substituted 5-dibenzofuran-4-yl-group.

9. The process of claim 3, wherein Z is an optionally substituted 1-benzofuran-7-yl group or an optionally substituted 5-dibenzofuran-4-yl group.

10. The process of claim 3, wherein no more than two of $R^1$ to $R^4$ include a fused cyclic structure.

11. The process of claim 3, wherein only one of $R^1$, $R^2$, $R^3$, and $R^4$ includes a fused cyclic structure.

12. The process of claim 3, wherein groups $R^1$ to $R^4$ that are not the fused cyclic structure as claimed in claim 1 are phenyl groups which are optionally substituted.

13. The process of claim 3, wherein X is selected from the group consisting of an organic linking group, an inorganic linking group comprising either a single- or two-atom linker spacer; and a group comprising dimethylmethylene, ethane-1,2-diyl, ethene-1,2-diyl, propane-1,2-diyl, propane-1,3-diyl, cyclopropane-1,1-diyl, cyclopropane-1,2-diyl, butane-2,3-diyl, cyclobutane-1,2-diyl, cyclopentane-1,2-diyl, cyclohexane-1,2-diyl, cyclohexane-1,1-diyl, 1,2-phenylene, naphthalene-1,8-diyl, phenanthrene-9,10-diyl, phenanthrene-4,5-diyl, 9,10-anthracene-diyl, 1,2-catecholate, 1,2-diarylhydrazine-1,2-diyl (—N(Ar)—N(Ar)— where Ar is an aryl group), 1,2-dialkylhydrazine-1,2-diyl (—N(Alk)-N(Alk)- where Alk is an alkyl or a cycloalkyl group), 1-alkyl-2-arylhydrazine-1,2-diyl (—N(Alk)-N(Ar)— where Alk is an alkyl or a cycloalkyl group and Ar is an aryl group), —N(R')—X$^1$—N(R")— where R' and R" are independently alkyl, cycloalkyl or aryl groups and X$^1$ is a hydrocarbylene group, —B(R$^5$)—, —Si(R$^5$)$_2$—, —P(R$^5$)— and —N(R$^5$)— where R$^5$ is a hydrocarbyl group, an organoheteryl group or a heterohydrocarbyl group.

14. The process of claim 3, wherein X consists of —N(R$^6$)—, —N(R$^6$)—N(R$^7$)—, —C(R$^{8a}$)(R$^{8b}$)—N(R$^6$)— or a hydrocarbylene, where R$^6$ and R$^7$ are independently a hydrocarbyl group, a heterohydrocarbyl group or an organoheteryl group and R$^{8a}$ and R$^{8b}$ are independently a hydrogen, a hydrocarbyl group, a heterohydrocarbyl group or an organoheteryl group.

15. The process of claim 3 where X consists of —N(R$^9$)—, where R$^9$ is a hydrocarbyl group, a heterohydrocarbyl group or an organoheteryl group.

16. The process of claim 1, wherein no more than two of $R^1$ to $R^4$ include a fused cyclic structure.

17. The process of claim 1, wherein only one of $R^1$, $R^2$, $R^3$, and $R^4$ includes a fused cyclic structure.

18. The process of claim 1, wherein groups $R^1$ to $R^4$ that are not the fused cyclic structure as claimed in claim 1 are phenyl groups which are optionally substituted.

19. The process of claim 1, wherein X is selected from the group consisting of an organic linking group, an inorganic linking group comprising either a single- or two-atom linker spacer; and a group comprising dimethylmethylene, ethane-1,2-diyl, ethene-1,2-diyl, propane-1,2-diyl, propane-1,3-diyl, cyclopropane-1,1-diyl, cyclopropane-1,2-diyl, butane-2,3-diyl, cyclobutane-1,2-diyl, cyclopentane-1,2-diyl, cyclohexane-1,2-diyl, cyclohexane-1,1-diyl, 1,2-phenylene, naphthalene-1,8-diyl, phenanthrene-9,10-diyl, phenanthrene-4,5-diyl, 9,10-anthracene-diyl, 1,2-catecholate, 1,2-diarylhydrazine-1,2-diyl (—N(Ar)—N(Ar)— where Ar is an aryl group), 1,2-dialkylhydrazine-1,2-diyl (—N(Alk)-N(Alk)- where Alk is an alkyl or a cycloalkyl group), 1-alkyl-2-arylhydrazine-1,2-diyl (—N(Alk)-N(Ar)— where Alk is an alkyl or a cycloalkyl group and Ar is an aryl group), —N(R')—X$^1$—N(R")— where R' and R" are independently alkyl, cycloalkyl or aryl groups and X$^1$ is a hydrocarbylene group, —B(R$^5$)—, —Si(R$^5$)$_2$—, —P(R$^5$)— and —N(R$^5$)— where R$^5$ is a hydrocarbyl group, an organoheteryl group or a heterohydrocarbyl group.

20. The process of claim 1, wherein X consists of —N(R$^6$)—, —N(R$^6$)—N(R$^7$)—, —C(R$^{8a}$)(R$^{8b}$)—Nr(R$^6$)— or a hydrocarbylene, where R$^6$ and R$^7$ are independently a hydrocarbyl group, a heterohydrocarbyl group or an organoheteryl group and R$^{8a}$ and R$^{8b}$ are independently a hydrogen, a hydrocarbyl group, a heterohydrocarbyl group or an organoheteryl group.

21. The process of claim 1 where X consists of —N(R$^9$)—, where R$^9$ is a hydrocarbyl group, a heterohydrocarbyl group or an organoheteryl group.

* * * * *